United States Patent [19]

Iwata et al.

[11] Patent Number: 5,565,363
[45] Date of Patent: Oct. 15, 1996

[54] REAGENT COMPOSITION FOR MEASURING IONIC STRENGTH OR SPECIFIC GRAVITY OF AQUEOUS SOLUTION SAMPLES

[75] Inventors: Kenji Iwata; Masako Shiojiri; Nobuyuki Tokioka, all of Amagasaki, Japan

[73] Assignee: Wako Pure Chemical Industries, Ltd., Osaka, Japan

[21] Appl. No.: 962,563

[22] Filed: Oct. 19, 1992

[30] Foreign Application Priority Data

Oct. 21, 1991 [JP] Japan ................................. 3-301011

[51] Int. Cl.$^6$ .......................... G01N 9/00; G01N 33/84; G01N 33/52
[52] U.S. Cl. ................ 436/2; 436/74; 436/163; 436/169; 436/79; 422/56; 422/57; 422/82.09; 422/82.05
[58] Field of Search ................ 422/56, 57, 82.5, 422/82.09, 69; 436/74, 163, 169, 2, 79, 88, 66, 68

[56] References Cited

U.S. PATENT DOCUMENTS

| | | | |
|---|---|---|---|
| 3,533,749 | 10/1970 | Kleinman | 436/88 |
| 3,558,278 | 1/1971 | Louderback et al. | 436/88 |
| 3,884,637 | 5/1975 | Gindler | 23/230 B |
| 4,015,462 | 4/1977 | Greyson et al. | 73/32 R |
| 4,318,709 | 3/1982 | Falb et al. | 23/230 R |
| 4,340,565 | 7/1982 | Kitajima et al. | 422/56 |
| 4,376,827 | 3/1983 | Stiso et al. | 436/2 |
| 4,473,650 | 9/1984 | Wang | 436/2 |
| 4,532,216 | 7/1985 | Wang | 436/2 |
| 4,649,123 | 3/1987 | Charlton et al. | 436/79 |
| 4,822,743 | 4/1989 | Wegrzyn | 436/3 |
| 4,921,807 | 5/1990 | Pak | 436/18 |
| 4,956,301 | 9/1990 | Ismail et al. | 436/87 |
| 4,992,381 | 2/1991 | Cram et al. | 436/74 |
| 5,055,407 | 10/1991 | Lau et al. | 436/2 |
| 5,064,615 | 11/1991 | Mangold | 422/56 |
| 5,106,752 | 4/1992 | Mangold et al. | 436/2 |
| 5,124,266 | 6/1992 | Coryn et al. | 436/86 |
| 5,126,275 | 6/1992 | Hatch et al. | 436/169 |
| 5,215,924 | 6/1993 | Rittersdorf et al. | 436/68 |

FOREIGN PATENT DOCUMENTS

| | | |
|---|---|---|
| 0023631A1 | 2/1981 | European Pat. Off. . |
| 0023631 | 2/1981 | European Pat. Off. . |
| 0114315A3 | 8/1984 | European Pat. Off. . |
| 0114316A2 | 8/1984 | European Pat. Off. . |
| 0349934A2 | 1/1990 | European Pat. Off. . |
| 0349843A3 | 1/1990 | European Pat. Off. . |
| 0418169 | 3/1991 | European Pat. Off. . |
| 417821 | 3/1991 | European Pat. Off. . |
| 0418169A2 | 3/1991 | European Pat. Off. . |
| 513564 | 4/1992 | European Pat. Off. . |
| 0513564A2 | 11/1992 | European Pat. Off. . |
| 120843 | 7/1984 | Japan . |
| 59-133208 | 7/1984 | Japan . |
| 62-95462 | 5/1987 | Japan . |
| 3-103196 | 4/1991 | Japan . |
| 3-103197 | 4/1991 | Japan . |
| 4-177164 | 6/1992 | Japan . |
| 4-177165 | 6/1992 | Japan . |
| 2037981 | 7/1980 | United Kingdom . |

OTHER PUBLICATIONS

Yamamoto, Spectrophotometric Method for the determination of Tonic surfactants by How–injection analysis with acidic dyes, Analytica Chimica Acta 246 (1991) 333–339.

Abstract of Yamamoto, Spectrophometric method for anionic surfactants on the basis of color change of Bromocresol Purple with a quaternary ammonium Ton, Bunseki Kagaku, 39(7), 393–7.

Sakai, Extraction–spectrophotometric determination of Benzethonium and Benzalkonium salts with Bromocresol Green and Quinine, Analytical Chimica Acta, 147(1983) 331–337.

Jurkeviciute et al, study of the interactions of scandium and chromazurol s with cetylpyridinium, cetyltrimethylammonium or carbethoxypentadecyltri–methylammonium bromide, Nov. 28, 1978, collect.

Czech. Chem. Commun., 44 (11), 3236–40, 1979 Gross, uncoupling of photophosphorylation Inhibition of proton binding by quaternary ammonium salts and zwitlevionic butters, 1971, Arch. Biochem. Biophys., 147 (1), 77–84.

*Primary Examiner*—Lyle A. Alexander
*Assistant Examiner*—Harold Pyon
*Attorney, Agent, or Firm*—Armstrong, Westerman, Hattori, McLeland & Naughton

[57] ABSTRACT

A reagent composition comprising (a) one or more pH buffers, (b) one or more pH indicators, and (c) one or more surfactants as a sensitizer, is suitable for measuring ionic strength or specific gravity of aqueous solution samples such as urine rapidly and precisely.

29 Claims, No Drawings

REAGENT COMPOSITION FOR MEASURING IONIC STRENGTH OR SPECIFIC GRAVITY OF AQUEOUS SOLUTION SAMPLES

BACKGROUND OF THE INVENTION

The present invention relates to a reagent composition for measuring ionic strength or specific gravity of aqueous solution samples, a test device obtained by impregnating or coating such a reagent composition into or on a carrier, and a process for using such a reagent composition or a test device for the measurement.

The specific gravity of urine is now directly measured by processes using, a urine gravimeter, a pycnometer, a refractometer, etc. These processes almost provide necessary precision. But the apparatuses used therefor require much time and cost for correcting scales and cleaning so as to maintain the required precision, accompanied with various inconvenience. Further, a quantity of urine sample is necessary at the time of measurement, but sometimes the amount may be scant. In addition, bubbles at the liquid surface and capillarity make the readout of scales difficult.

On the other hand, there have been developed and partially put into practical use a process for measuring a change of color tone or absorbance caused by mixing urine and a reagent solution by the naked eye or a colorimeter, and a process for easily measuring a specific gravity or ionic strength of urine comprising dipping a specimen shaped into a stick form, and judging a change of color tone with the naked eye. The latter process can be carried out not only by the measurement of absorbance using a colorimeter or the naked eye judgement by a comparison of color charts, but also by the measurement of reflectance using a light emitting diode. Further, the process of using the test device has an advantage of simultaneously measuring other items of urine examination such as glucose, hemoglobin, protein, leucocyte, bilirubin, pH, ascorbic acid, urobilinogen, ketones, a nitrite, etc.

Various processes for measuring ionic strength or specific gravity of liquid samples by the measurement of changes of color tone or absorbance are disclosed as follows.

U.S. Pat. No. 4,015,462 discloses a process comprising holding microcapsules encapsulating colorants on a carrier matrix, contacting the microcapsules with a solution of low osmotic pressure to raise the inner pressure of microcapsules, to distend and rupture the microcapsules and to release the colorants, and applying a phenomenon of changing the color of matrix (the depth of color being proportional to the specific gravity of the solution).

Japanese Patent Unexamined Publication No. 55-101047 (GB 2037981) discloses a process for measuring the ionic strength or specific gravity by using a test device containing a composition comprising a polyelectrolyte such as polyacrylic acid or polyvinylamine, which is neutralized at least at about 50%, and a pH indicator.

Japanese Patent Unexamined Publication No. 56-21064 (EP 23631) discloses a process using a composition comprising a strongly acidic or strongly basic polyelectrolyte, a buffering substance capable of maintaining the pH at least about pH 5.5, and a means for indicating a pH, the polyelectrolyte being polystyrene sulfonate, polyvinyl sulfate, or polyvinylbenzyl ammonium chloride.

Japanese Patent Unexamined Publication No. 59-133207 (U.S. Pat. No. 4,473,650) discloses a reagent composition comprising a weakly basic polyelectrolyte polymer neutralized with a strong organic acid, and an indicator, said polyelectrolyte polymer being polyethyleneimine, polyvinylamine, polyaminostyrene, or a copolymer of the monomers constituting the polyelectrolyte polymer.

Japanese Patent Unexamined Publication No. 59-133208 (U.S. Pat. No. 4,532,216) discloses a composition comprising a weakly basic polyelectrolyte polymer containing at least one carboxyl group in the form of an ammonium salt and an indicator.

Japanese Patent Unexamined Publication No. 2-66451 (U.S. Pat. No. 5,106,752, U.S. Pat. No. 5,064,615) discloses a composition comprising at least one pH buffer (without a polyelectrolyte polymer) or at least one pH buffer and/or at least one complex-forming agent, and at least one pH indicator.

Japanese Patent Unexamined Publication No. 3-100461 (EP 418169) discloses a process using a dye or dye precursor wherein an ionic concentration relates to a solubility.

These processes and compositions have been developed as processes for measuring ionic strength or specific gravity of liquid samples using a test device, and partly put into practical uses. These processes measure one or more special components among Na, K, etc., which are factors of specific gravity of urine. Thus, the obtained data does not always agree to the specific gravity completely. Further, when samples with various levels of specific gravities are measured, there is a common problem in that since the color difference change of colored tone is small in a high specific gravity region, it is difficult to judge with the naked eye. In addition, according to these processes, since a coloring rate is relatively slow, it requires undesirably a long time for the measurement, when a number of samples are to be automatically judged optically.

SUMMARY OF THE INVENTION

It is an object of the present invention to provide a reagent composition for measuring ionic strength or specific gravity of liquid samples, overcoming disadvantages of prior art processes. The reagent composition of the present invention is capable of detecting changes of specific gravity caused by Na, K, Ca, Mg, etc., large in changes in color difference of colored tone, easy to judge by the naked eye in the measurement of ionic strength and specific gravity of liquid samples such as urine, and is able to easily and automatically judge optically a number of samples due to fast coloring rate.

It is another object of the present invention to provide a test device obtained by impregnating a carrier or support or coating a carrier or support with the above-mentioned reagent composition.

It is a further object of the present invention to provide a process for measuring ionic strength or specific gravity of liquid samples using such a reagent composition or such a test device.

The present invention provides a reagent composition for measuring an ionic strength or a specific gravity of an aqueous solution sample comprising (a) one or more pH buffers, (b) one or more pH indicators, and (c) one or more surfactants as a sensitizer.

The present invention also provides a process for measuring an ionic strength or a specific gravity of an aqueous solution sample, which comprises mixing the aqueous solution sample with the reagent composition mentioned above, and detecting changes of pH of the solution and changes of the degree of dissociation of the pH indicator.

The present invention further provides a test device for measuring an ionic strength or a specific gravity of an aqueous solution sample obtained by impregnating an absorptive carrier with the reagent composition mentioned above or coating the reagent composition mentioned above on a film, followed by drying.

The present invention still provides a process for measuring an ionic strength or a specific gravity of an aqueous solution sample, which comprises dipping the test device mentioned above in an aqueous solution sample to impregnate the solution sample thereinto, taking the test device out of the aqueous solution sample, and detecting changes of pH of the test device and changes of the degree of dissociation of the pH indicator, after a predetermined time, e.g. 10 seconds to 5 or 6 minutes.

The present invention still further provides a process for measuring an ionic strength or a specific gravity of an aqueous solution sample, which comprises dropping an aqueous solution sample on the test device mentioned above, and detecting changes of pH of the test device and changes of the degree of dissociation of pH indicator, after a predetermined time.

DESCRIPTION OF THE PREFERRED EMBODIMENTS

According to the present invention, the measurement of ionic strength and specific gravity of liquid samples is improved remarkably by using a surfactant as a sensitizer in place of a polyelectrolyte and a complex-forming agent in the prior art processes for measuring ionic strengths or specific gravities by detecting changes of pH. Further, according to the present invention, various substances which are large in color difference of colored tone and can be factors for constituting the specific gravity, can be measured as many as possible, the detection can be carried out by the naked eye even in a high specific gravity region with a wide detection range, and a number of samples can easily and automatically judged optically due to fast coloring rate.

In the present invention, the reagent composition for measuring an ionic strength or specific gravity of aqueous solution sample comprises (a) one or more pH buffers, (b) one or more pH indicators, and (c) one or more surfactants as a sensitizer.

The surfactant has functions for not only improving solubility and wetting, but also, surprisingly suppressing the dissociation of pH indicator in contrast to a prior art process wherein the dissociation is accelerated by the addition of a salt. As a result, a change of absorbance (OD) of the pH indicator accompanied with pH change of buffer by the addition of a salt can be increased. Thus, the present invention has been accomplished.

The pH of a buffer solution comprising a buffer having the degree of dissociation of 1.00 or less, more strictly 0.9 or less, is generally changed depending on increase of ionic strength. For example, in the case of a buffer solution of a combination of a weak acid and a strong base, the pH is lowered by the addition of a strong electrolyte. On the other hand, in the case of a buffer solution of a combination of a strong acid and a weak base, the pH is raised by the addition of a strong electrolyte.

Ordinary pH indicators, particularly those of triphenylmethane series, are accelerated in dissociation even at the same pH by increasing the ionic strength. Thus, when this pH change is measured by using a pH indicator, and a buffer solution of a combination of a weak acid and a strong base is used at the time of measuring ionic strength or specific gravity from absorbance changing values ($\Delta OD$), the pH lowering of the buffer solution and the accelerating effect for dissociation of the pH indicator are set off to show a lower absorbance changing value ($\Delta OD$) than a practical value, or sometimes, a negative absorbance value ($-\Delta OD$), resulting in showing no practical value.

But when a surfactant is added to such a system, not only the acceleration of dissociation of pH indicator is suppressed to obtain the absorbance changing value ($\Delta OD$) corresponding to the pH change, but also the absorbance changing value ($\Delta OD$) more than the pH changing value ($\Delta pH$) due to sensitizing effect can be obtained.

As the pH buffer (a), there can be used those which can be used in the pH range of preferably 3.0 to 10.0, more preferably 4.0 to 9.0 and change the pH by the change of concentration caused by the addition of a strong electrolyte such as a chloride, e.g. sodium chloride, potassium chloride, etc., or a sulfate. Preferable examples are a phosphate buffer, a borate buffer, a citrate buffer, a tris(hydroxymethyl)-aminomethane-maleate buffer [tris-maleate buffer], bis(2-hydroxyethyl)iminotris(hydroxymethyl)methane buffer [bistris buffer], etc.

When a phosphate buffer or bistris buffer is used together with a weak acid such as boric acid, citric acid, or the like, or a salt thereof, the production of a salt such as sodium chloride can preferably be prevented at the time of adjusting pH.

Examples of the acid are boric acid, citric acid, malonic acid, maleic acid, metaphosphoric acid, tartaric acid, oxalic acid, phosphoric acid, phthalic acid, etc.

Examples of salts of these acids are a sodium salt thereof, a potassium salt thereof, a lithium salt thereof, an ammonium salt thereof.

As the pH indicator (b), there can be used those which have a transition interval in a pH changing area of the pH buffer. Particularly preferable pH indicators are triphenylmethane series wherein the dissociation is accelerated by the increase of ionic strength. Preferable examples of the pH indicator are bromothymol blue, bromocresol purple, thymol blue, phenol red, chlorophenol red, bromocresol green, etc. It is possible to use methyl red, etc. as the pH indicator other than the triphenylmethane series.

These pH indicators can be used singly or as a mixture thereof. For example, co-use of bromothymol blue and one or more other pH indicator can enlarge a change of colored tone and a transition interval. Such co-use is preferable from the viewpoint of practical use. Examples of the other pH indicator usable together with bromothymol blue are thymol blue, phenol red, and the like pH indicators.

As the surfactant (c), there can be used those having a function of suppressing dissociation of pH indicator, said dissociation being accelerated by increasing ionic strength. Examples of the surfactant are anionic surfactants, cationic surfactants, amphoteric surfactant, and nonionic surfactants.

Examples of anionic surfactants are higher alcohol sulfonates or sulfates, e.g. sodium dodecylsulfate (SDS), lithium dodecylsulfate, sodium dodecylbenzenesulfonate (SDBS), sodium 1-dodecanesulfonate, sodium diisooctylsulfosuccinate (SDOSS), sodium octylsulfate, etc. These anionic surfactants are preferably used together with a pH buffer of neutral to alkaline (pH 6 to 10).

Examples of cationic surfactants are quaternary ammonium salts containing one or more alkyl groups having 7 or more carbon atoms, usually 30 or less carbon atoms, for example, myristyltrimethylammonium bromide (MTAB), cetyltrimethylammonium bromide (CTAB), octadecyltrimethylammonium chloride, dodecyltrimethylammonium chloride, cetyltrimethylammonium chloride, lauryltrimethylammonium chloride, etc.; quaternary ammonium salts having a phenyl group such as benzalconium chloride, tetradecyldimethylbenzylammonium chloride, octadecyldimethylbenzylammonium chloride, lauryldimethylbenzylammonium chloride, etc.; quaternary ammonium salts having a pyridyl group such as laurylpyridinium chloride, cetylpyridinium chloride stearylamidomethylpyridinium chloride etc. These quaternary ammonium salts can be used in any pH range.

When a quaternary ammonium salt containing only alkyl groups having 6 or less carbon atoms is used, there is a tendency to fail to show the effect of the present invention.

Examples of amphoteric surfactants are alkyl betaines such as lauryl dimethyl betaine, stearyl betaine, etc.; 2-lauryl-N-carboxymethyl-N-hydroxyethylimidazolinium betaine, etc. These amphoteric surfactants are preferably used together with a pH buffer of a neutral area (pH 6 to 8).

Examples of nonionic surfactants are polyoxyethylene alkyl phenyl ethers such as polyoxyethylene (8) octyl phenyl ether, polyoxyethylene (10) octyl phenyl ether, etc; polyoxyethylene alkyl esters such as polyoxyethylene (20) sorbitane monolaurate, polyoxyethylene sorbitane monooleate, polyoxyethylene sorbitane monopalmitate, polyoxyethylene sorbitane monostearate, polyoxyethylene sorbitane trioleate, etc. These nonionic surfactants are preferably used together with a pH buffer of a neutral area (pH 6 to 8).

Preferable combinations of the three components (a) pH buffers, (b) pH indicators and (c) surfactants of the reagent composition of the present invention are shown in Table 1.

TABLE 1

| | pH buffer | pH indicator | Surfactant |
|---|---|---|---|
| (1) | pH buffer of pH 3.5 to 5.5 (e.g. citrate, phosphate-citrate, etc.) | pH indicator having a transition interval in the pH range of 3.5 to 5.5 (e.g. chlorophenol red, bromocresol green, methyl red, etc.) | Cationic surfactant (e.g. MTAB, CTAB, benzalconium chloride, lauryl-pyridinium chloride, cetylpyridinium chloride, etc.) |
| (2) | pH buffer of pH 5.5 to 8.5 (e.g. phosphate, phosphate-borate, tris-maleate, bistris-borate, etc.) | pH indicator having a transition interval in the pH range of 5.5 to 8.5 (e.g. bromothymol blue, bromo-cresol purple, methyl red, bromothymol blue + thymol blue, bromothymol blue + phenol red, etc.) | Cationic surfactant (e.g. MTAB, CTAB, benzalconium chloride, lauryl-pyridinium chloride, cetylpyridinium chloride, etc.) |
| (3) | pH buffer of pH 5.5 to 8.5 (e.g. phosphate, phosphate-borate, tris-maleate, bistris-borate, etc.) | pH indicator having a transition interval in the pH range of 5.5 to 8.5 (e.g. bromothymol blue, bromo-cresol purple, methyl red, bromothymol blue + thymol blue, bromothymol blue + phenol red, etc.) | Anionic surfactant (e.g. SDS, SDOSS, SDBS, etc.) |
| (4) | pH buffer of pH 5.5 to 8.5 (e.g. phosphate, phosphate-borate, tris-maleate, bistris-borate, etc.) | pH indicator having a transition interval in the pH range of 5.5 to 8.5 (e.g. bromothymol blue, bromo-cresol purple, methyl red, bromothymol blue + thymol blue, bromothymol blue + phenol red, etc.) | Amphoteric surfactant (e.g. lauryl dimethyl betaine, 2-lauryl-N-carboxymethyl-N-hydroxyethyl imidazolinium betaine, etc.) |
| (5) | pH buffer of pH 5.5 to 8.5 (e.g. phosphate, phosphate-borate, tris-maleate, bistris-borate, etc.) | pH indicator having a transition interval in the pH range of 5.5 to 8.5 (e.g. bromothymol blue, bromo-cresol purple, methyl red, bromothymol blue + thymol blue, bromothymol blue + phenol red, etc.) | Nonionic surfactant (e.g. sorbitane monolaurate, polyoxyethylene (10) octyl phenyl ether, polyoxyethylene (20) sorbitane monolaurate, etc.) |
| (6) | pH buffer of pH 8.5 to 10.0 (e.g. borate, phosphate-borate, etc.) | pH indicator having a transition interval in the pH range of 8.5 to 10.0 (e.g. thymol blue, etc.) | Cationic surfactant (e.g. MTAB, CTAB, benzalconium chloride, lauryl-pyridinium chloride, cetylpyridinium chloride, etc.) |

The reagent composition of the present invention can be used most effectively in the form of a test device, and can also be used in the form of a liquid, a powder, a tablet, etc.

The reagent composition of the present invention comprises (a) one or more pH buffers in an amount of usually 45% to 99.89% by weight, preferably 95.0% to 99.8% by weight, more preferably 98.0% to 99.7% by weight, (b) one or more pH indicators in an amount of usually 0.01% to 25% by weight, preferably 0.02% to 0.5% by weight, more preferably 0.03% to 0.3% by weight, and (c) one or more surfactants in an amount of usually 0.1% to 30.0% by weight, preferably 0.2% to 3.0 weight, more preferably 0.3% to 1.5% by weight, in the form of liquid, including for impregnation or coating, a total being 100% by weight.

In the case of the test device, a liquid reagent composition of the present invention comprising (a) one or more pH buffers in an amount of usually 45% to 99.89% by weight, preferably 60% to 98.5% by weight, (b) one or more pH indicators in an amount of usually 0.01% to 25% by weight, preferably 1% to 15% by weight, and (c) one or more surfactants in an amount of usually 0.1% to 30% by weight, preferably 0.3% to 20% by weight, a total being 100% by weight, is impregnated into a carrier or coated on a carrier so as to give a test device, for example, a filter paper (30 cm$^2$) containing (a) one or more pH buffers in an amount of 1 to 120 mg (liquid amount of 1 to 900 mM), preferably 5 to 75 mg (liquid amount of 20 to 500 mM), (b) one or more pH indicators in an amount of 0.3 to 1 mg (dried weight), preferably 0.4 to 0.8 mg (dried weight), and (c) one or more surfactants in an amount of 0.1 to 1 mg (dried weight), preferably 0.2 to 0.8 mg (dried weight).

When the reagent composition is used in the form of a liquid, an aqueous solution sample and the reagent composition are mixed and changes of pH of the solution and changes of the degree of dissociation of pH indicator are detected. The changes of pH and changes of the degree of dissociation of pH indicator can easily be detected by measuring absorbance change ($\Delta$OD).

When the reagent composition of the present invention is used as a test device, the reagent composition is impregnated into a carrier such as an absorptive carrier or coated on a carrier such as a film to form a test device, which is dipped in an aqueous solution sample to impregnate the sample thereinto, taken out of the solution, followed by detection of changes of pH of the test device and changes of the degree of dissociation of pH indicator after a predetermined time, e.g. 10 seconds to 5 or 6 minutes.

The changes of pH and changes of the degree of dissociation of pH indicator can be judged with the naked eye by comparing the color of colored test device after a predetermined time with a color tone of standard color tone table prepared by the same procedure as mentioned above using a solution of known ionic strength or known specific gravity, or can be detected by optically measuring reflectance of the color of test device after a predetermined time.

Another process of using the test device comprises dropping an aqueous liquid sample on the test device, and measuring the color of test device with the naked eye, or measuring the reflectance optically.

The test device containing the reagent composition can be used in various shapes.

That is, individual components of the reagent composition, other reagent and a binder are dissolved in water, an organic solvent or a mixed solvent obtained therefrom to prepare a reagent solution, which is impregnated into an absorptive carrier one or more (several) times, or coated (e.g. brushed or sprayed) on a carrier film one or more (several) times, followed by drying to give a test sheet. The test sheet is cut into a suitable size, and fixed on a suitable support to prive the test device in the form of stick, tape, or the like.

As the binder, there can be used polyvinyl pyrrolidone, polyvinyl alcohol, polyethylene glycol, hydroxypropyl methyl cellulose, gum arabic, gelatin, ethyl cellulose, etc.

As the absorptive carrier, there can be used porous carriers such as cellulose fabric filter paper, cloth, nonwoven fabric, paper, synthetic fabric filter paper, etc.

As the film for coating the reagent solution, there can be used a synthetic film, an aluminum laminated film, etc.

As the support for holding the absorptive carrier or the film, there can be used a sheet of synthetic high polymer such as polyvinyl chloride, polyester, polyethylene terephthalate, polystyrene, polyvinyl acetal, polypropylene, polyvinylidene chloride, or the like; a thick sheet of paper coated with the synthetic high polymers mentioned above.

The size, thickness, etc. of the absorptive carrier, film and support are not limited particularly, and sufficient when conventionally used ones are used. The absorptive carrier or the film can be held on the support by a method using a conventional adhesive, a method using an adhesive tape, etc.

The concentration of pH buffer in the reagent solution, the impregnating solution, or the coating solution (hereinafter referred to as "reagent or impregnating solution") is usually 1 to 900 mM, preferably 5 to 300 mM, when the reagent composition of the present invention is used in the form of a solution or test device.

The concentration of pH indicator in the reagent or impregnating solution is usually 0.0005 to 0.5 w/v %, preferably 0.001 to 0.2 w/v %.

The concentration of surfactant in the reagent or impregnating solution is usually 0.001 to 2.0 w/v %, preferably 0.005 to 1.0 w/v %.

As the aqueous solution sample, there can be used urine, cerebrospinal fluid, ascites, pleural effusion, etc.

The present invention is explained in detail referring to Examples and Comparative Examples.

EXAMPLE 1

| | |
|---|---|
| Disodium hydrogen phosphate.12 hydrate | 1.07 g |
| Sodium dihydrogen phosphate.dihydrate | 0.02 g |
| Sodium dodecylsulfate | 0.07 g |
| Bromothymol blue | 0.10 g |
| Distilled water | 100 ml |

A reagent solution having the above-mentioned composition was prepared and impregnated into a filter paper for chromatography (30 cm$^2$, hereinafter the same size was used), followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a urine sample having a specific gravity measured by using a pycnometer and listed in Table 2, a different color shown in Table 2 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. Further, the coloring was exhibited with high sensitivity. Thus, the sensitivity increasing effect of the surfactant was admitted.

TABLE 2

| Specific gravity | Color of test device | Reflectance (%) (635 nm) |
|---|---|---|
| 1.000 | Bluish green | 13.6 |
| 1.010 | Green | 22.1 |
| 1.020 | Yellowish green | 31.5 |
| 1.030 | Pale yellowish green | 40.1 |
| 1.040 | Dark yellow | 46.1 |

EXAMPLE 2

| | |
|---|---|
| Disodium hydrogen phosphate.12 hydrate | 1.07 g |
| Boric acid | 0.09 g |
| Sodium diisooctylsulfosuccinate | 0.1 g |

| | |
|---|---|
| Bromothymol blue | 0.09 g |
| Thymol blue | 0.04 g |
| Distilled water | 100 ml |

A reagent solution having the above-mentioned composition was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a urine sample having a specific gravity measured by using a pycnometer and listed in Table 3, a different color shown in Table 3 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. Further, the coloring was exhibited with high sensitivity as in Example 1. Thus, the sensitivity increasing effect of the surfactant was admitted.

TABLE 3

| Specific gravity | Color of test device | Reflectance (%) (635 nm) |
|---|---|---|
| 1.000 | Bluish green | 14.1 |
| 1.010 | Green | 24.2 |
| 1.020 | Yellowish green | 32.4 |
| 1.030 | Pale yellowish green | 41.4 |
| 1.040 | Dark yellow | 48.3 |

COMPARATIVE EXAMPLE 1

| | |
|---|---|
| Disodium hydrogen phosphate.12 hydrate | 1.07 g |
| Boric acid | 0.09 g |
| Bromothymol blue | 0.09 g |
| Thymol blue | 0.04 g |
| Distilled water | 100 ml |

A reagent solution having the above-mentioned composition (the same as the composition of Example 2 except for not using the surfactant) was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a urine sample having a specific gravity measured by using a pycnometer and listed in Table 4, a different color shown in Table 4 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. But, the coloring sensitivity was lower than that of Example 2.

TABLE 4

| Specific gravity | Color of test device | Reflectance (%) (635 nm) |
|---|---|---|
| 1.000 | Bluish green | 16.1 |
| 1.010 | Dark green | 20.7 |
| 1.020 | Green | 27.5 |
| 1.030 | Pale green | 31.0 |
| 1.040 | Yellowish green | 34.9 |

EXAMPLE 3

| | |
|---|---|
| Disodium hydrogen phosphate.12 hydrate | 1.07 g |
| Boric acid | 0.09 g |
| Sodium dodecylsulfate | 0.07 g |
| Bromothymol blue | 0.09 g |
| Thymol blue | 0.04 g |
| Distilled water | 100 ml |

A reagent solution having the above-mentioned composition was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a urine sample having a specific gravity measured by using a pycnometer and listed in Table 5, a different color shown in Table 5 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. Further, the coloring was exhibited with high sensitivity as in Examples 1 and 2. Thus, the sensitivity increasing effect of the surfactant was admitted.

TABLE 5

| Specific gravity | Color of test device | Reflectance (%) (635 nm) |
|---|---|---|
| 1.000 | Bluish green | 14.4 |
| 1.010 | Green | 23.9 |
| 1.020 | Yellowish green | 31.5 |
| 1.030 | Pale yellowish green | 40.1 |
| 1.040 | Yellow | 47.2 |

EXAMPLE 4

| | |
|---|---|
| Disodium hydrogen phosphate.12 hydrate | 1.07 g |
| Boric acid | 0.09 g |
| Sodium dodecylbenzenesulfonate | 0.09 g |
| Bromothymol blue | 0.09 g |
| Thymol blue | 0.04 g |
| Distilled water | 100 ml |

A reagent solution having the above-mentioned composition was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a urine sample having a specific gravity measured by using a pycnometer and listed in Table 6, a different color shown in Table 6 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. Further, the coloring was exhibited with high sensitivity as in Examples 1 to 3. Thus, the sensitivity increasing effect of the surfactant was admitted.

TABLE 6

| Specific gravity | Color of test device | Reflectance (%) (635 nm) |
|---|---|---|
| 1.000 | Bluish green | 14.5 |
| 1.010 | Green | 22.7 |
| 1.020 | Yellowish green | 30.5 |
| 1.030 | Pale yellowish green | 40.1 |
| 1.040 | Yellow | 47.0 |

EXAMPLE 5

| | |
|---|---|
| Disodium hydrogen phosphate.12 hydrate | 1.07 g |
| Boric acid | 0.09 g |
| Sorbitane monolaurate | 0.10 g |
| Bromothymol blue | 0.09 g |
| Thymol blue | 0.04 g |
| Distilled water | 100 ml |

A reagent solution having the above-mentioned composition was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm) using a double-adhesive tape to give a test-device.

When the resulting test device was dipped in a urine sample having a specific gravity measured by using a pycnometer and listed in Table 7, a different color shown in Table 7 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. Further, the coloring was exhibited with high sensitivity as in Examples 1 to 4. Thus, the sensitivity increasing effect of the surfactant was admitted.

TABLE 7

| Specific gravity | Color of test device | Reflectance (%) (635 nm) |
|---|---|---|
| 1.000 | Bluish green | 16.7 |
| 1.010 | Green | 24.9 |
| 1.020 | Yellowish green | 33.8 |
| 1.030 | Pale yellowish green | 39.9 |
| 1.040 | Pale yellowish brown | 46.8 |

EXAMPLE 6

| | |
|---|---|
| Disodium hydrogen phosphate.12 hydrate | 1.07 g |
| Boric acid | 0.09 g |
| Polyoxyethylene (10) octylphenyl ether | 0.10 g |
| Bromothymol blue | 0.09 g |
| Thymol blue | 0.04 g |
| Distilled water | 100 ml |

A reagent solution having the above-mentioned composition was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a urine sample having a specific gravity measured by using a pycnometer and listed in Table 8, a different color shown in Table 8 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. Further, the coloring was exhibited with high sensitivity as in Examples 1 to 5. Thus, the sensitivity increasing effect of the surfactant was admitted.

TABLE 8

| Specific gravity | Color of test device | Reflectance (%) (635 nm) |
|---|---|---|
| 1.000 | Bluish green | 20.9 |
| 1.010 | Green | 28.8 |
| 1.020 | Yellowish green | 39.4 |
| 1.030 | Pale yellowish green | 46.7 |
| 1.040 | Dark yellow | 51.2 |

EXAMPLE 7

| | |
|---|---|
| Disodium hydrogen phosphate.12 hydrate | 1.07 g |
| Boric acid | 0.09 g |
| Polyoxyethylene (20) sorbitane monolaurate | 0.05 g |
| Bromothymol blue | 0.09 g |
| Thymol blue | 0.04 g |
| Distilled water | 100 ml |

A reagent solution having the above-mentioned composition was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a urine sample having a specific gravity measured by using a pycnometer and listed in Table 9, a different color shown in Table 9 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. Further, the coloring was exhibited with high sensitivity as in Examples 1 to 6. Thus, the sensitivity increasing effect of the surfactant was admitted.

TABLE 9

| Specific gravity | Color of test device | Reflectance (%) (635 nm) |
|---|---|---|
| 1.000 | Bluish green | 17.0 |
| 1.010 | Green | 24.8 |
| 1.020 | Yellowish green | 32.8 |
| 1.030 | Pale yellowish green | 40.4 |
| 1.040 | Dark yellow | 47.0 |

EXAMPLE 8

| | |
|---|---|
| Disodium hydrogen phosphate.12 hydrate | 1.07 g |
| Boric acid | 0.09 g |
| Lauryl dimethyl betaine | 0.10 g |
| Bromothymol blue | 0.09 g |
| Thymol blue | 0.04 g |
| Distilled water | 100 ml |

A reagent solution having the above-mentioned composition was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a urine sample having a specific gravity measured by using a pycnometer and listed in Table 10, a different color shown in Table 10 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. Further, the coloring was exhibited with high sensitivity as in Examples 1 to 7. Thus, the sensitivity increasing effect of the surfactant was admitted.

TABLE 10

| Specific gravity | Color of test device | Reflectance (%) (635 nm) |
|---|---|---|
| 1.000 | Dark green | 18.9 |
| 1.010 | Yellowish green | 26.2 |
| 1.020 | Pale yellowish green | 33.6 |
| 1.030 | Yellowish brown | 40.6 |
| 1.040 | Dark yellow | 47.9 |

EXAMPLE 9

| | |
|---|---|
| Polyvinyl pyrrolidone (K-30) | 40 g |
| Disodium hydrogen phosphate.12 hydrate | 1.07 g |
| Boric acid | 0.09 g |
| Sodium dodecylsulfate | 0.07 g |
| Bromothymol blue | 0.09 g |
| Thymol blue | 0.04 g |
| Distilled water | 100 ml |
| (adjusted to pH 7.75 with 20% NaOH solution) | |

A reagent solution having the above-mentioned composition was prepared and coated on a plastic film, followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a urine sample having a specific gravity measured by using a pycnometer and listed in Table 11, a different color shown in Table 11 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. Further, the coloring was exhibited with high sensitivity as in Examples 1 to 8. Thus, the sensitivity increasing effect of the surfactant was admitted.

TABLE 11

| Specific gravity | Color of test device | Reflectance (%) (635 nm) |
|---|---|---|
| 1.000 | Bluish green | 17.5 |
| 1.010 | Green | 28.9 |
| 1.020 | Yellowish green | 35.1 |
| 1.030 | Pale yellowish green | 40.4 |
| 1.040 | Dark yellow | 46.7 |

EXAMPLE 10

| | |
|---|---|
| Sodium dihydrogen phosphate.dihydrate | 3.51 g |
| Boric acid | 0.70 g |
| Sodium hydroxide | 0.75 g |
| Sodium diisooctylsulfosuccinate | 0.05 g |
| Polyethylene glycol-4000 | 0.05 g |
| Bromothymol blue | 0.09 g |
| Thymol blue | 0.04 g |
| Ethyl alcohol | 12.5 ml |
| Distilled water | 87.5 ml |

A reagent solution having the above-mentioned composition was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a urine sample having a specific gravity measured by using a pycnometer and listed in Table 12, a different color shown in Table 12 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. Further, the coloring was exhibited with high sensitivity as in Examples 1 to 9. Thus, the sensitivity increasing effect of the surfactant was admitted.

TABLE 12

| Specific gravity | Color of test device | Reflectance (%) (635 nm) |
|---|---|---|
| 1.000 | Dark green | 21.5 |
| 1.010 | Pale green | 31.5 |
| 1.020 | Pale yellowish green | 41.9 |
| 1.030 | Pale yellowish brown | 48.0 |
| 1.040 | Pale yellow | 55.5 |

EXAMPLE 11

| | |
|---|---|
| Disodium hydrogen phosphate.12 hydrate | 1.07 g |
| Sodium dihydrogen phosphate.dihydrate | 0.02 g |
| Sodium dodecylsulfate | 0.07 g |
| Bromothymol blue | 0.09 g |
| Thymol blue | 0.04 g |
| Distilled water | 100 ml |

A reagent solution having the above-mentioned composition was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm)

using a double-adhesive tape to give a test device.

When the resulting test device was dipped in a urine sample having a specific gravity measured by using a pycnometer and listed in Table 13, a different color shown in Table 13 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. Further, the coloring was exhibited with high sensitivity as in Examples 1 to 10. Thus, the sensitivity increasing effect of the surfactant was admitted.

TABLE 13

| Specific gravity | Color of test device | Reflectance (%) (635 nm) |
| --- | --- | --- |
| 1.000 | Bluish green | 14.3 |
| 1.010 | Green | 22.7 |
| 1.020 | Yellowish green | 32.0 |
| 1.030 | Pale yellowish green | 41.2 |
| 1.040 | Yellow | 47.2 |

EXAMPLE 12

| | |
| --- | --- |
| Disodium hydrogen phosphate.12 hydrate | 1.07 g |
| Sodium dihydrogen phosphate.dihydrate | 0.02 g |
| Sodium dodecylsulfate | 0.07 g |
| Bromothymol blue | 0.05 g |
| Phenol red | 0.05 g |
| Distilled water | 100 ml |

A reagent solution having the above-mentioned composition was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a urine sample having a specific gravity measured by using a pycnometer and listed in Table 14, a different color shown in Table 14 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. Further, the coloring was exhibited with high sensitivity as in Examples 1 to 11. Thus, the sensitivity increasing effect of the surfactant was admitted.

TABLE 14

| Specific gravity | Color of test device | Reflectance (%) (635 nm) |
| --- | --- | --- |
| 1.000 | Dark reddish violet | 26.1 |
| 1.010 | Dark reddish orange | 36.3 |
| 1.020 | Reddish orange | 45.2 |
| 1.030 | Pale reddish orange | 49.6 |
| 1.040 | Orange | 55.1 |

EXAMPLE 13

| | |
| --- | --- |
| Citric acid.monohydrate | 1.05 g |
| Sodium hydroxide | 0.2 g |
| Myristyltrimethylammonium bromide | 0.05 g |
| Bromocresol green | 0.1 g |
| Distilled water | 100 ml |
| (Adjusted to pH 4.0) | |

A reagent solution having the above-mentioned composition was prepared and impregnated into a filter paper for chromatography, followed by drying at 55° to 65° C. The resulting test sheet was cut into a rectangle of 5 mm×6 mm and adhered to a polyvinyl chloride sheet (5 mm×11 cm) using a double-adhesive tape to give a test device.

When the resulting test device was dipped in a urine sample having a specific gravity measured by using a pycnometer and listed in Table 15, a different color shown in Table 15 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. Further, the coloring was exhibited with high sensitivity as in Examples 1 to 12. Thus, the sensitivity increasing effect of the surfactant was admitted.

TABLE 15

| Specific gravity | Color of test device | Reflectance (%) (635 nm) |
| --- | --- | --- |
| 1.000 | Clear green | 25.7 |
| 1.010 | Dark yellowish green | 33.7 |
| 1.020 | Yellowish green | 40.9 |
| 1.030 | Pale yellowish green | 46.2 |
| 1.040 | Yellow | 52.4 |

COMPARATIVE EXAMPLE 2

| | |
| --- | --- |
| Citric acid.monohydrate | 1.05 g |
| Sodium hydroxide | 0.2 g |
| Bromocresol green | 0.1 g |
| Distilled water | 100 ml |
| (Adjusted to pH 4.0) | |

A reagent solution having the above-mentioned composition (the same composition as in Example 13 except for not using the surfactant) was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a urine sample having a specific gravity measured by using a pycnometer and listed in Table 16, a different color shown in Table 16 was obtained. Further, values of reflectance after 30 seconds using a reflectance measuring apparatus (Pretester-RM 405, mfd. by Wako Pure Chemical Industries, Ltd.) showed a proportional relationship to individual specific gravity ranked values. But the coloring sensitivity was lower than that of Example 13.

TABLE 16

| Specific gravity | Color of test device | Reflectance (%) (635 nm) |
| --- | --- | --- |
| 1.000 | Pale green | 29.9 |
| 1.010 | Yellowish green | 33.3 |
| 1.020 | Yellowish green | 34.2 |
| 1.030 | Pale yellowish green | 40.0 |
| 1.040 | Pale yellowish green | 41.5 |

EXAMPLE 14

| | |
| --- | --- |
| Tris(hydroxymethyl)aminomethane | 2.42 g |
| Maleic acid | 2.32 g |
| Sodium hydroxide | 0.79 g |
| Sodium dodecylsulfate | 0.02 g |
| Bromothymol blue | 2 mg |
| Distilled water | 100 ml |

A reagent solution having the above-mentioned composition was prepared. To 5 ml of the reagent solution, 0.4 ml of each urine sample having a specific gravity as listed in Table 17 and measured using a pycnometer was added and mixed. The resulting mixture was subjected to measurement of changes of absorbance using a spectrophotometer (Hitachi 557 type, mfd. by Hitachi, Ltd.). The results were as shown in Table 17. As shown in Table 17, the measured values of absorbance showed a proportional relationship to individual specific gravity ranked values. Further the absorbance change was large and the sensitivity increasing effect of the surfactant was admitted.

TABLE 17

| Specific gravity | Absorbance (615 nm) | Absorbance change |
| --- | --- | --- |
| 1.000 | 0.550 | — |
| 1.010 | 0.527 | 0.023 |
| 1.020 | 0.501 | 0.049 |
| 1.030 | 0.480 | 0.070 |
| 1.040 | 0.456 | 0.094 |

COMPARATIVE EXAMPLE 3

| | |
| --- | --- |
| Tris(hydroxymethyl)aminomethane | 2.42 g |
| Maleic acid | 2.32 g |
| Sodium hydroxide | 0.79 g |
| Bromothymol blue | 2 mg |
| Distilled water | 100 ml |

A reagent solution having the above-mentioned composition (the same composition as in Example 14 except for not containing the surfactant) was prepared. To 5 ml of the reagent solution, 0.4 ml of each urine sample having a specific gravity as listed in Table 18 and measured using a pycnometer was added and mixed. The resulting mixture was subjected to measurement of changes of absorbance using a spectrophotometer (Hitachi 557 type, mfd. by Hitachi, Ltd.). The results were as shown in Table 18. As shown in Table 18, the measured values of absorbance showed almost no proportional relationship to individual specific gravity ranked values. The sensitivity was very low compared with Example 14.

TABLE 18

| Specific gravity | Absorbance (615 nm) | Absorbance change |
| --- | --- | --- |
| 1.000 | 0.628 | — |
| 1.010 | 0.629 | 0.001 |
| 1.020 | 0.628 | 0.000 |
| 1.030 | 0.630 | 0.002 |
| 1.040 | 0.630 | 0.002 |

EXAMPLE 15

| | |
| --- | --- |
| Sodium dihydrogen phosphate.dihydrate | 2.61 g |
| Boric acid | 1.03 g |
| Sodium hydroxide | 0.50 g |
| Sodium dodecylsulfate | 0.02 g |
| Bromothymol blue | 2 mg |
| Distilled water | 100 ml |

A reagent solution having the above-mentioned composition was prepared. To 5 ml of the reagent solution, 0.4 ml of each urine sample having a specific gravity as listed in Table 19 and measured using a pycnometer was added and mixed. The resulting mixture was subjected to measurement of changes of absorbance using a spectrophotometer (Hitachi 557 type, mfd. by Hitachi, Ltd.). The results were as shown in Table 19. As shown in Table 19, the measured values of absorbance showed a proportional relationship to individual specific gravity ranked values. Further the absorbance change was large. Thus, the sensitivity increasing effect of the surfactant was admitted, as in the case of the test device.

TABLE 19

| Specific gravity | Absorbance (615 nm) | Absorbance change |
| --- | --- | --- |
| 1.000 | 0.598 | — |
| 1.010 | 0.567 | 0.031 |
| 1.020 | 0.529 | 0.069 |
| 1.030 | 0.494 | 0.104 |
| 1.040 | 0.462 | 0.136 |

COMPARATIVE EXAMPLE 4

| | |
| --- | --- |
| Sodium dihydrogen phosphate.dihydrate | 2.61 g |
| Boric acid | 1.03 g |
| Sodium hydroxide | 0.50 g |
| Bromothymol blue | 2 mg |
| Distilled water | 100 ml |

A reagent solution having the above-mentioned composition (the same composition as in Example 15 except for not containing the surfactant) was prepared. To 5 ml of the reagent solution, 0.4 ml of each urine sample having a specific gravity as listed in Table 20 and measured using a pycnometer was added and mixed. The resulting mixture was subjected to measurement of changes of absorbance using a spectrophotometer (Hitachi 557 type, mfd. by Hitachi, Ltd.). The results were as shown in Table 20. As shown in Table 20, the measured values of absorbance showed almost no proportional relationship to individual specific gravity ranked values. The sensitivity was very low compared with Example 15.

TABLE 20

| Specific gravity | Absorbance (615 nm) | Absorbance change |
| --- | --- | --- |
| 1.000 | 0.596 | — |
| 1.010 | 0.592 | 0.004 |
| 1.020 | 0.585 | 0.011 |
| 1.030 | 0.583 | 0.013 |
| 1.040 | 0.579 | 0.017 |

EXAMPLE 16

| | |
| --- | --- |
| Citric acid.monohydrate | 1.41 g |
| Sodium hydroxide | 0.52 g |
| Myristyltrimethylammonium bromide | 0.02 g |
| Chlorophenol red | 5 mg |
| Distilled water | 100 ml |

A reagent solution having the above-mentioned composition was prepared. To 5 ml of the reagent solution, 0.4 ml of each urine sample having a specific gravity as listed in Table 21 and measured using a pycnometer was added and mixed. The resulting mixture was subjected to measurement of changes of absorbance using a spectrophotometer (Hitachi 557 type, mfd. by Hitachi, Ltd.). The results were as shown in Table 21. As shown in Table 21, the measured values of absorbance showed a proportional relationship with individual specific gravity ranked values. Further the absorbance change was large and the same high sensitivity as in Example 15 was also shown. Thus, the sensitivity increasing effect of the surfactant was admitted.

TABLE 21

| Specific gravity | Absorbance (615 nm) | Absorbance change |
| --- | --- | --- |
| 1.000 | 0.801 | — |
| 1.010 | 0.771 | 0.030 |
| 1.020 | 0.739 | 0.062 |
| 1.030 | 0.706 | 0.095 |
| 1.040 | 0.671 | 0.130 |

EXAMPLE 17

| | |
| --- | --- |
| Boric acid | 1.24 g |
| Potassium chloride | 1.49 g |
| Sodium hydroxide | 0.37 g |
| Myristyltrimethylammonium bromide | 0.02 g |
| Thymol blue | 2.5 mg |
| Distilled water | 100 ml |

A reagent solution having the above-mentioned composition was prepared. To 5 ml of the reagent solution, 0.4 ml of each urine sample having a specific gravity as listed in Table 22 and measured using a pycnometer was added and mixed. The resulting mixture was subjected to measurement of changes of absorbance using a spectrophotometer (Hitachi 557 type, mfd. by Hitachi, Ltd.). The results were as shown in Table 22. As shown in Table 22, the measured values of absorbance showed a proportional relationship to individual specific gravity ranked values. Further the absorbance change was large and the same high sensitivity as in Examples 15 and 16 was also shown. Thus, the sensitivity increasing effect of the surfactant was admitted.

TABLE 22

| Specific gravity | Absorbance (615 nm) | Absorbance change |
| --- | --- | --- |
| 1.000 | 0.668 | — |
| 1.010 | 0.613 | 0.055 |
| 1.020 | 0.564 | 0.104 |
| 1.030 | 0.529 | 0.139 |
| 1.040 | 0.496 | 0.172 |

EXAMPLE 18

| | |
| --- | --- |
| Sodium dihydrogen phosphate.dihydrate | 0.54 g |
| Disodium hydrogen phosphate.12 hydrate | 2.35 g |
| Polyoxyethylene (10) octylphenyl ether | 12.5 mg |
| Bromothymol blue | 4 mg |
| Distilled water | 100 ml |

A reagent solution having the above-mentioned composition was prepared. To 5 ml of the reagent solution, 0.4 ml of each urine sample having a specific gravity as listed in Table 23 and measured using a pycnometer was added and mixed. The resulting mixture was subjected to measurement of changes of absorbance using a spectrophotometer (Hitachi 557 type, mfd. by Hitachi, Ltd.). The results were as shown in Table 23. As shown in Table 23, the measured values of absorbance showed a proportional relationship to individual specific gravity ranked values. Further the absorbance change was large and the same high sensitivity as in Examples 15 to 17 was also shown. Thus, the sensitivity increasing effect of the surfactant was admitted.

TABLE 23

| Specific gravity | Absorbance (615 nm) | Absorbance change |
| --- | --- | --- |
| 1.000 | 0.910 | — |
| 1.010 | 0.884 | 0.026 |
| 1.020 | 0.860 | 0.050 |
| 1.030 | 0.829 | 0.081 |
| 1.040 | 0.804 | 0.106 |

EXAMPLE 19

| | |
| --- | --- |
| Sodium dihydrogen phosphate.dihydrate | 0.54 g |
| Disodium hydrogen phosphate.12 hydrate | 2.35 g |
| Cetyltrimethylammonium bromide | 0.02 g |
| Bromothymol blue | 3.8 mg |
| Distilled water | 100 ml |

A reagent solution having the above-mentioned composition was prepared. To 5 ml of the reagent solution, 0.4 ml of each urine sample having a specific gravity as listed in Table 24 and measured using a pycnometer was added and mixed. The resulting mixture was subjected to measurement of changes of absorbance using a spectrophotometer (Hitachi 557 type, mfd. by Hitachi, Ltd.). The results were as shown in Table 24. As shown in Table 24, the measured values of absorbance showed a proportional relationship to individual specific gravity ranked values. Further the absorbance change was large and the same high sensitivity as in Examples 15 to 18 was also shown. Thus, the sensitivity increasing effect of the surfactant was admitted.

TABLE 24

| Specific gravity | Absorbance (600 nm) | Absorbance change |
|---|---|---|
| 1.000 | 1.230 | — |
| 1.010 | 1.135 | 0.095 |
| 1.020 | 1.047 | 0.183 |
| 1.030 | 0.958 | 0.272 |
| 1.040 | 0.867 | 0.363 |

COMPARATIVE EXAMPLE 5

| | |
|---|---|
| Sodium dihydrogen phosphate.dihydrate | 0.54 g |
| Disodium hydrogen phosphate.12 hydrate | 2.35 g |
| Tetrabutylammonium bromide | 20 mg |
| Bromothymol blue | 3.8 mg |
| Distilled water | 100 ml |

A reagent solution having the above-mentioned composition (tetrabutylammonium bromide having 4 alkyl groups having 4 carbon atoms being used in place of cetyltrimethylammonium bromide used in Example 19 having one alkyl group having 16 carbon atoms and three alkyl groups having 1 carbon atom) was prepared. To 5 ml of the reagent solution, 0.4 ml of each urine sample having a specific gravity as listed in Table 25 and measured using a pycnometer was added and mixed. The resulting mixture was subjected to measurement of changes of absorbance using a spectrophotometer (Hitachi 557 type, mfd. by Hitachi, Ltd.). The results were as shown in Table 25. As shown in Table 25, the sensitivity was remarkably low compared with Example 19.

TABLE 25

| Specific gravity | Absorbance (600 nm) | Absorbance change |
|---|---|---|
| 1.000 | 1.053 | — |
| 1.010 | 1.039 | 0.014 |
| 1.020 | 1.025 | 0.028 |
| 1.030 | 0.011 | 0.042 |
| 1.040 | 0.997 | 0.056 |

When tetrabutylammonium hydroxide, an example of quaternary ammonium hydroxides disclosed in Japanese Patent Unexamined Publication No. 59-133208=U.S. Pat. No. 4,532,216 used as a neutralizing agent for polyelectrolyte, is used in place of the tetrabutylammonium bromide, the same undesirable results as mentioned above were obtained.

EXAMPLE 20

| | |
|---|---|
| Bis(2-hydroxyethyl)iminotris(hydroxymethyl)methane | 3.94 g |
| Boric acid | 0.07 g |
| Lauryl dimethyl betaine | 0.02 g |
| Bromothymol blue | 4 mg |
| Distilled water | 100 ml |

A reagent solution having the above-mentioned composition was prepared. To 5 ml of the reagent solution, 0.4 ml of each urine sample having a specific gravity as listed in Table 26 and measured using a pycnometer was added and mixed. The resulting mixture was subjected to measurement of changes of absorbance using a spectrophotometer (Hitachi 557 type, mfd. by Hitachi, Ltd.). The results were as shown in Table 26. As shown in Table 26, the measured values of absorbance showed a proportional relationship to individual specific gravity ranked values. Further the absorbance change was large and the same high sensitivity as in Examples 15 to 19 was also shown. Thus, the sensitivity increasing effect of the surfactant was admitted.

TABLE 26

| Specific gravity | Absorbance (600 nm) | Absorbance change |
|---|---|---|
| 1.000 | 0.720 | — |
| 1.010 | 0.755 | 0.035 |
| 1.020 | 0.796 | 0.076 |
| 1.030 | 0.839 | 0.119 |
| 1.040 | 0.880 | 0.160 |

EXAMPLE 21

| | |
|---|---|
| Sodium dihydrogen phosphate.dihydrate | 0.54 g |
| Disodium hydrogen phosphate.12 hydrate | 2.35 g |
| Benzalconium chloride | 40 mg |
| Bromothymol blue | 3.8 mg |
| Distilled water | 100 ml |

A reagent solution having the above-mentioned composition was prepared. To 5 ml of the reagent solution, 0.4 ml of each urine sample having a specific gravity as listed in Table 27 and measured using a pycnometer was added and mixed. The resulting mixture was subjected to measurement of changes of absorbance using a spectrophotometer (Hitachi 557 type, mfd. by Hitachi, Ltd.). The results were as shown in Table 27. As shown in Table 27, the measured values of absorbance showed a proportional relationship to individual specific gravity ranked values. Further the absorbance change was large and the same high sensitivity as in Examples 15 to 20 was also shown. Thus, the sensitivity increasing effect of the surfactant was admitted.

TABLE 27

| Specific gravity | Absorbance (600 nm) | Absorbance change |
|---|---|---|
| 1.000 | 1.007 | — |
| 1.010 | 0.925 | 0.082 |
| 1.020 | 0.845 | 0.162 |
| 1.030 | 0.764 | 0.243 |
| 1.040 | 0.685 | 0.822 |

EXAMPLE 22

| | |
|---|---|
| Sodium dihydrogen phosphate.dihydrate | 0.54 g |
| Disodium hydrogen phosphate.12 hydrate | 2.35 g |
| Cetylpyridinium chloride | 10 mg |
| Bromothymol blue | 2.3 mg |
| Distilled water | 100 ml |

A reagent solution having the above-mentioned composition was prepared. To 5 ml of the reagent solution, 0.4 ml of each urine sample having a specific gravity as listed in Table 28 and measured using a pycnometer was added and mixed. The resulting mixture was subjected to measurement of changes of absorbance using a spectrophotometer (Hitachi 557 type, mfd. by Hitachi, Ltd.). The results were as shown in Table 28. As shown in Table 28, the measured values of absorbance showed a proportional relationship to individual specific gravity ranked values. Further the absorbance change was large and the same high sensitivity as in Examples 15 to 21 was also shown. Thus, the sensitivity increasing effect of the surfactant was admitted.

TABLE 28

| Specific gravity | Absorbance (600 nm) | Absorbance change |
|---|---|---|
| 1.000 | 0.836 | — |
| 1.010 | 0.787 | 0.049 |
| 1.020 | 0.737 | 0.099 |
| 1.030 | 0.691 | 0.145 |
| 1.040 | 0.646 | 0.190 |

EXAMPLE 23

| | |
|---|---|
| Disodium hydrogen phosphate.12 hydrate | 1.07 g |
| Boric acid | 0.09 g |
| Sodium diisooctylsulfosuccinate | 0.1 g |
| Bromothymol blue | 0.09 g |
| Thymol blue | 0.04 g |
| Distilled water | 100 ml |

A reagent solution having the above-mentioned composition was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a sodium chloride aqueous solution having a concentration listed in Table 29, a different color shown in Table 29 was obtained. Further, values of reflectance after 30 seconds using a reflectance measuring apparatus (Pretester-RM 405, mfd. by Wako Pure Chemical Industries, Ltd.) showed a proportional relationship to individual concentration ranked values i.e. ionic strength. Further, the coloring was exhibited with high sensitivity. Thus, the sensitivity increasing effect of the surfactant was admitted.

TABLE 29

| Concentration of NaCl (M) | Color of test device | Reflectance (%) (635 nm) |
|---|---|---|
| 0 | Bluish green | 14.1 |
| 0.25 | Green | 24.2 |
| 0.50 | Yellowish green | 32.4 |
| 0.75 | Pale yellowish green | 41.4 |
| 1.00 | Yellow | 48.3 |

COMPARATIVE EXAMPLE 6

| | |
|---|---|
| Disodium hydrogen phosphate.12 hydrate | 1.07 g |
| Boric acid | 0.09 g |
| Bromothymol blue | 0.09 g |
| Thymol blue | 0.04 g |
| Distilled water | 100 ml |

A reagent solution having the above-mentioned composition (the same composition as in Example 23 except for not using the surfactant) was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a sodium chloride aqueous solution having a concentration listed in Table 30, a different color shown in Table 30 was obtained. Further, values of reflectance after 30 seconds using a reflectance measuring apparatus (Pretester-RM 405, mfd. by Wako Pure Chemical Industries, Ltd.) showed a proportional relationship to individual concentration ranked values i.e. ionic strength. But the coloring sensitivity was lower than that of Example 23.

TABLE 30

| Concentration of NaCl (M) | Color of specimen | Reflectance (%) (635 nm) |
|---|---|---|
| 0 | Bluish green | 16.1 |
| 0.25 | Dark green | 20.7 |
| 0.50 | Green | 27.5 |
| 0.75 | Pale green | 31.0 |
| 1.00 | Yellowish green | 34.9 |

EXAMPLE 24

| | |
|---|---|
| Disodium hydrogen phosphate.12 hydrate | 1.07 g |
| Sodium dihydrogen phosphate.dihydrate | 0.02 g |
| Sodium dodecylsulfate | 0.07 g |
| Bromothymol blue | 0.10 g |
| Distilled water | 100 ml |

A reagent solution having the above-mentioned composition was prepared and impregnated into a filter paper for chromatography, followed by drying at 55° to 65° C. The resulting test sheet was cut into a rectangle of 5 mm×6 mm and adhered to a polyvinyl chloride sheet (6 mm×11 cm) using a double-adhesive tape to give a test device.

When the resulting test device was dipped in a sodium chloride aqueous solution having a concentration listed in Table 31, a different color shown in Table 31 was obtained. Further, values of reflectance after 30 seconds using a reflectance measuring apparatus (Pretester-RM 405, mfd. by Wako Pure Chemical Industries, Ltd.) showed a proportional relationship to individual concentration ranked values i.e. ionic strength. Further, the coloring was exhibited with high sensitivity as in Example 23. Thus, the sensitivity increasing effect of the surfactant was admitted.

TABLE 31

| Concentration of NaCl (M) | Color of specimen | Reflectance (%) (635 nm) |
|---|---|---|
| 0 | Bluish green | 13.6 |
| 0.25 | Green | 22.1 |
| 0.50 | Yellowish green | 31.5 |
| 0.75 | Pale yellowish green | 40.1 |
| 1.00 | Dark Yellow | 46.1 |

As is clear from the above results, the reagent compositions of Examples 1 to 24 show excellent coloring with high sensitivity.

In contrast, the reagents compositions of Comparative Examples 1 to 6 are low in the coloring sensitivity.

As mentioned above, the reagent composition for measuring ionic strength or specific gravity of aqueous solution samples according to the present invention comprises (a) one or more pH buffers, (b) one or more pH indicators, and (c) one or more surfactants as a sensitizer. By using such a reagent composition, problems caused by using known reagent compositions for measuring ionic strength or specific gravity, e.g., small in absorbance changes, poor in reproducibility, small in color difference change of colored tone, difficult in judgement with the naked eye at the time of measuring ionic strength and specific gravity of a liquid sample such as urine, long time being required for automatically judging optically a number of samples due to slow coloring rate, etc. are solved by the present invention. Thus, the present invention contributes to this art very much.

What is claimed is:

1. A reagent composition for measuring an ionic strength or a specific gravity of an aqueous solution sample, said reagent composition consisting essentially of
    (a) 1–900 mM of one or more pH buffers having a pH of 5.5 to 8.5,
    (b) 0.0005–0.5 w/v % of one or more pH indicators having a transition interval in the pH range of 5.5 to 8.5, and
    (c) 0.001–2.0 w/v % of one or more surfactants selected from the group consisting of anionic, nonionic and amphoteric surfactants, and having a function of a sensitizer, said composition being suitable for detecting changes of pH of the aqueous solution and changes of the degree of dissociation of the pH indicator.

2. A reagent composition according to claim 1, wherein the one or more pH buffers is present in an amount of from 45% to 99.89% by weight, the one or more pH indicators is present in an amount of from 0.01% to 25% by weight, and the one or more surfactants is present in an amount of from 0.1% to 30.0% by weight.

3. A reagent composition according to claim 1, wherein the one or more pH buffers is present in an amount of from 95.0% to 99.8% by weight, the one or more pH indicators is present in an amount of from 0.02% to 0.5% by weight, and the one or more surfactants is present in an amount of from 0.2% to 3.0% by weight.

4. A reagent composition according to claim 1, wherein the one or more pH buffers is present in an amount of from 98.0% to 99.7% by weight, the one or more pH indicators is present in an amount of from 0.03% to 0.3% by weight, and the one or more surfactants is present in an amount of from 0.3% to 1.5% by weight.

5. A reagent composition according to claim 1, wherein the pH buffer has a pH of 5.5 to 8.5, the pH indicator has a transition interval in the pH range of 5.5 to 8.5 and the surfactant is one or more anionic surfactants.

6. A reagent composition according to claim 1, wherein the pH buffer has a pH of 5.5 to 8.5, the pH indicator has a transition interval in the pH range of 5.5 to 8.5 and the surfactant is one or more amphoteric surfactants.

7. A reagent composition according to claim 1, wherein the pH buffer has a pH of 5.5 to 8.5, the pH indicator has a transition interval in the pH range of 5.5 to 8.5 and the surfactant is one or more nonionic surfactants.

8. A reagent composition according to claim 1, wherein the concentration of pH buffer is 5–300 mM, the concentration of pH indicator is 0.001–0.2 w/v %, and the concentration of surfactant is 0.005–1.0 w/v %.

9. A test device for measuring an ionic strength or a specific gravity of an aqueous solution sample, comprising a porous carrier or film impregnated or coated with a reagent composition consisting essentially of
    (a) 1–900 mM of one or more pH buffers having a pH of 3.5 to 10.0,
    (b) 0.0005–0.5 w/v % of one or more pH indicators having a transition interval in the pH range of 3.5 to 10.0, and
    (c) 0.001–2.0 w/v % of one or more surfactants selected from the group consisting of anionic, nonionic and amphoteric surfactants, and having a function of a sensitizer,
    said composition being suitable for detecting changes of pH of the aqueous solution and changes of the degree of dissociation of the pH indicator,
    said carrier being dried after being impregnated or coated with said reagent composition.

10. A test device according to claim 9, wherein the pH buffer has a pH of 5.5 to 8.5, the pH indicator has a transition interval in the pH range of 5.5 to 8.5 and the surfactant is one or more anionic surfactants.

11. A test device according to claim 9, wherein the pH buffer has a pH of 5.5 to 8.5, the pH indicator has a transition interval in the pH range of 5.5 to 8.5 and the surfactant is one or more amphoteric surfactants.

12. A test device according to claim 9, wherein the pH buffer has a pH of 5.5 to 8.5, the pH indicator has a transition interval in the pH range of 5.5 to 8.5 and the surfactant is one or more nonionic surfactants.

13. A test device according to claim 9, wherein the porous carrier is cellulose fabric filter paper, cloth, nonwoven fabric, paper, or synthetic fabric filter paper, and the film is a synthetic film or an aluminum laminated film.

14. A process for measuring an ionic strength or a specific gravity of an aqueous solution sample, which comprises
    mixing the aqueous solution sample with a reagent composition, said reagent composition consisting essentially of
    (a) 1–900 mM of one or more pH buffers having a pH of 3.5 to 10.0,
    (b) 0.0005–0.5 w/v % of one or more pH indicators having a transition interval in the pH range of 3.5 to 10.0, and
    (c) 0.001–2.0 w/v % of one or more surfactants selected from the group consisting of anionic, nonionic and amphoteric surfactants, and having a function of a sensitizer, said composition being suitable for detecting changes of pH of the aqueous solution and changes of the degree of dissociation of the pH indicator, and
    detecting changes of pH of the solution and changes of the degree of dissociation of the pH indicator.

15. A process according to claim 14, wherein the changes of pH and the changes of the degree of dissociation are detected by measuring absorption changes.

16. A process according to claim 14, wherein the pH buffer has a pH of 5.5 to 8.5, the pH indicator has a transition interval in the pH range of 5.5 to 8.5 and the surfactant is one or more anionic surfactants.

17. A process according to claim 14, wherein the pH buffer has a pH of 5.5 to 8.5, the pH indicator has a transition interval in the pH range of 5.5 to 8.5 and the surfactant is one or more amphoteric surfactants.

18. A process according to claim 14, wherein the pH buffer has a pH of 5.5 to 8.5, the pH indicator has a transition interval in the pH range of 5.5 to 8.5 and the surfactant is one or more nonionic surfactants.

19. A process for measuring an ionic strength or a specific gravity of an aqueous solution sample, which comprises
    dipping a test device in an aqueous solution sample to impregnate the solution sample thereinto, taking said test device out of the aqueous solution sample, and detecting changes of pH of the test device and changes of the degree of dissociation of the pH indicator, after a predetermined time, said test device comprising a carrier impregnated or coated with a reagent composition consisting essentially of
  (a) 1–900 mM of one or more pH buffers having a pH of 3.5 to 10.0,
  (b) 0.0005–0.5 w/v % of one or more pH indicators having a transition interval in the pH range of 3.5 to 10.0, and
  (c) 0.001–2.0 w/v % of one or more surfactants selected from the group consisting of anionic, nonionic and amphoteric surfactants, and having a function of a sensitizer, said composition being suitable for detecting changes of pH of the aqueous solution and changes of the degree of dissociation of the pH indicator, said carrier being dried after being impregnated or coated with said reagent composition.

20. A process according to claim 19, wherein the changes of pH and the changes of the degree of dissociation are judged by coloring of the test device with the naked eye, or detected by measuring a reflectance optically.

21. A process according to claim 19, wherein the pH buffer has a pH of 5.5 to 8.5, the pH indicator has a transition interval in the pH range of 5.5 to 8.5 and the surfactant is one or more anionic surfactants.

22. A process according to claim 19, wherein the pH buffer has a pH of 5.5 to 8.5, the pH indicator has a transition interval in the pH range of 5.5 to 8.5 and the surfactant is one or more amphoteric surfactants.

23. A process according to claim 19, wherein the pH buffer has a pH of 5.5 to 8.5, the pH indicator has a transition interval in the pH range of 5.5 to 8.5 and the surfactant is one or more nonionic surfactants.

24. A process for measuring an ionic strength or a specific gravity of an aqueous solution sample, which comprises dropping an aqueous solution sample on a test device said test device comprising a carrier impregnated or coated with a reagent composition consisting essentially of
  (a) 1–900 mM of one or more pH buffers having a pH of 3.5 to 10.0,
  (b) 0.0005–0.5 w/v % of one or more pH indicators having a transition interval in the pH range of 3.5 to 10.0, and
  (c) 0.001–2.0 w/v % of one or more surfactants selected from the group consisting of anionic, nonionic and amphoteric surfactants, and having a function of a sensitizer, said composition being suitable for detecting changes of pH of the aqueous solution and changes of the degree of dissociation of the pH indicator, said carrier being dried after being impregnated or coated with said reagent composition, and detecting changes of pH of the test device and changes of the degree of dissociation of pH indicator, after a predetermined time.

25. A process according to claim 24, wherein the changes of pH and the changes of the degree of dissociation are judged by coloring of the test device with the naked eye, or detected by measuring a reflectance optically.

26. A process according to claim 14, 19 or 24, wherein the concentration of pH buffer is 5–300 mM, the concentration of pH indicator is 0.001–0.2 w/v %, and the concentration of surfactant is 0.005–1.0 w/v %.

27. A process according to claim 24, wherein the pH buffer has a pH of 5.5 to 8.5, the pH indicator has a transition interval in the pH range of 5.5 to 8.5 and the surfactant is one or more anionic surfactants.

28. A process according to claim 24, wherein the pH buffer has a pH of 5.5 to 8.5, the pH indicator has a transition interval in the pH range of 5.5 to 8.5 and the surfactant is one or more amphoteric surfactants.

29. A process according to claim 24, wherein the pH buffer has a pH of 5.5 to 8.5, the pH indicator has a transition interval in the pH range of 5.5 to 8.5 and the surfactant is one or more nonionic surfactants.

* * * * *